United States Patent [19]

Edgren et al.

[11] Patent Number: 4,871,548

[45] Date of Patent: Oct. 3, 1989

[54] CONTROLLED RELEASE DOSAGE FORM COMPRISING DIFFERENT CELLULOSE ETHERS

[75] Inventors: David E. Edgren, El Granada; Judy A. Magruder, Palo Alto; Gurdish K. Bhatti, Fremont, all of Calif.

[73] Assignee: ALZA Corporation, Palo Alto, Calif.

[21] Appl. No.: 39,405

[22] Filed: Apr. 17, 1987

[51] Int. Cl.[4] ............................................... A61K 9/14
[52] U.S. Cl. ..................................... 424/488; 424/451; 424/464; 424/470
[58] Field of Search ............... 424/468, 469, 464, 470, 424/499, 488, 484

[56] References Cited

U.S. PATENT DOCUMENTS

| | | | |
|---|---|---|---|
| 4,167,558 | 9/1979 | Sheth et al. | 424/362 X |
| 4,369,172 | 1/1983 | Schor et al. | 424/362 X |
| 4,389,393 | 6/1983 | Schor et al. | 424/362 X |
| 4,553,973 | 11/1985 | Edgren | 424/473 X |

*Primary Examiner*—Thurman K. Page
*Attorney, Agent, or Firm*—Paul L. Sabatine; Edward L. Mandell; Steven F. Stone

[57] ABSTRACT

A dosage form is disclosed comprising a low number average molecular weight hydroxypropylmethylcellulose, a high number average molecular weight hydroxypropylmethylcellulose, and a beneficial drug.

3 Claims, 2 Drawing Sheets

CONTROLLED RELEASE DOSAGE FORM COMPRISING DIFFERENT CELLULOSE ETHERS

CROSS REFERENCE TO COPENDING APPLICATION

The patent application is copending with a patent application identified by Ser. No. 034,971, filed 4-6-87, now U.S. Pat. No. 4,786,503.

FIELD OF THE INVENTION

This invention concerns a controlled release dosage form. More specifically the invention relates to a dosage form comprising at least two different cellulose ethers and at lease one beneficial drug for administering the drug to a fluid environment of use. The dosage form comprises at least thirty weight percent (wt %) of the cellulose ethers.

BACKGROUND OF THE INVENTION

Tablets comprising a cellulose ether are known to the pharmaceutical drug delivery art. For example, tablets containing the cellulose ether hydroxypropylmethycellulose are known in U.S. Pat. Nos. 3,870,790; 4,140,755; 4,167,588; 4,226,849; 4,259,314; 4,357,469; 4,369,172; 4,389,393 and 4,540,566.

The tablets known to the prior art using the hydroxypropyl-methylcellulose ether often have certain disadvantages associated with their structure and with their use. For example, the mechanical integrity of some prior art tablets frequently is insufficient to provide both a sustained and a rate controlled release of a drug over a prolonged period of time in a moving fluid environment of use. The prior art tablets often exhibit insufficient mechanical integrity, that is the cohesive ability to stay together in a moving fluid environment such as the gastrointestinal tract, without prematurely breaking-up and without prematurely releasing all of its drug content. The above-mentioned desirable properties are not readily apparent in the prior art tablets, which appear to undergo substantial disintegration in a short time span, usually less than eight hours in a fluid environment of use.

Another disadvantage associated with the prior art tablets is that they exhibit an unwanted, variable, and difficult to reproduce a rate of release pattern. For example, prior art tablets comprising a small amount of a cellulose ether exhibit this behavior, such as by tablets consisting of less than five weight percent of a hydroxypropylmethylcellulose having a number average molecular weight greater than 50,000. The presence of the small amount of this high molecular weight polymeric ether in the tablet masks the release characteristic of other polymeric ethers in the tablets resulting in an erratic release pattern which is difficult to reproduce from batch to batch and from tablet to tablet.

Still other unacceptable disadvantages associated with the prior art tablets are that the tablets during their shelf-life can exhibit an unpredictable change in their release-rate characteristics; the prior art tablet when tested in an in vitro test that substantially reproduces the in vivo environment of the gastrointestinal tract often releases the drug at a greater rate of release in vivo than in vitro, which difference can be attributed to a premature disintegration of the prior art tablet; and the prior art tablet in a high fluid shear environment releases its drug too quickly, usually in less than six hours and these tablets therefore are not adapted to prolonged release.

Thus, in the light of the above presentation it will be appreciated by those versed in the dispensing art, that if a novel dosage form is made available to the medical and the pharmaceutical arts for dispensing a difficult to deliver drug free of the tribulation known to the prior art, such a dosage form would have a definite use and would also be a valuable contribution to the dispensing art. It will be further appreciated by those versed in the dispensing art that if a dosage form can be provided that (a) possesses a desirable rate of release and mechanical properties for dispensing a drug over a prolonged period of time, and which dosage form (b) can be manufactured at an economical cost, such a dosage form would have a positive and a practical value and it would also represent an advancement in the dispensing arts.

OBJECTS OF THE INVENTION

Accordingly, it is an immediate object of this invention to provide a novel dosage form for the rate controlled delivery of a beneficial drug to a biological fluid environment of use, and which unique dosage form represents an improvement and an advancement in the drug delivery arts.

Another object of this invention is to provide both a novel and a useful dosage form that substantially overcomes the difficulties associated with the tablets of the prior art.

Another object of the invention is to provide a dosage form comprising at least thirty weight percent of a nontoxic cellulosic ether formulation.

Another object of the invention is to provide a dosage form comprising at least two cellulose ethers that function together for enhancing the pharmaco-release kinetics of the dosage form.

Another object of the invention is to provide a novel dosage form that comprises a cellulose ether formulation, which cellulose ether formulation comprises a low number average molecular weight hydroxypropylmethylcellulose ether and a high number average molecular weight hydroxypropylmethylcellulose ether, which cellulose ether formulation operate as a unit in a moving fluid for controlling the rate of release of a beneficial drug from the dosage form.

Another object of this invention is to provide a dosage form comprising means for delivering a beneficial drug formulation that is difficult to deliver at meaningful rates and now can be delivered by the dosage form of this invention in a higher shear fluid environment of use at therapeutically useful rates over a prolonged period of time.

Another object of the present invention is to provide a dosage form comprising a beneficial drug formulation that can be from insoluble to very soluble in an aqueous fluid, and which drug formulation can be delivered by the dosage form of this invention comprising two different cellulose ethers at an in vitro rate of release that is substantially paralleled by the in vivo rate of drug release.

Another object of this invention is to provide a dosage form that can administer to a warm-blooded host a complete pharmaceutical regimen comprising very soluble or poorly soluble drugs, at a rate controlled by the dosage form and at a continuous rate for a particular time period, the use of which dosage form requires intervention only for initiation of the drug delivery regimen.

Another object of the present invention is to provide a dosage form of delivering a drug in the gastrointestinal tract that substantially avoids a premature disintegration and delivers a drug at a rate of dosage form release that corresponds to the rate of change of the integrity of the dosage form over a prolonged period of at least eight hours.

Another object of the invention is to provide a dosage form comprising a high loading up to 70 wt % of an aqueous soluble drug, which can be delivered at a controlled rate by the dosage form and which high loading of the insoluble drug could not be delivered by prior art and osmotic tablets.

Another object of the invention is to provide a dosage form comprising a low number molecular weight hydroxypropylmethylcellulose ether, a high number molecular weight hydroxypropylmethylcellulose ether and an optional hydroxypropylcellulose ether for delivering a beneficial drug to the gastrointestinal tract of an animal.

Other objects, features, aspects and advantages of the invention will be more apparent to those versed in the dispensing art from the following detailed specification taken in conjunction with the drawing figures and the accompanying claims.

BRIEF DESCRIPTION OF THE DRAWINGS

In the drawings, which are not drawn to scale but are set forth to illustrate various embodiments that can be provided by the invention, the drawing figures are as follows.

In the drawings and in the specifications like parts in related figures are identified by like numbers. The terms appearing earlier in the specification and in the drawings, as well as embodiments thereof, are further described elsewhere in this specification.

DETAILED DESCRIPTION OF THE DRAWINGS

Figure 1:
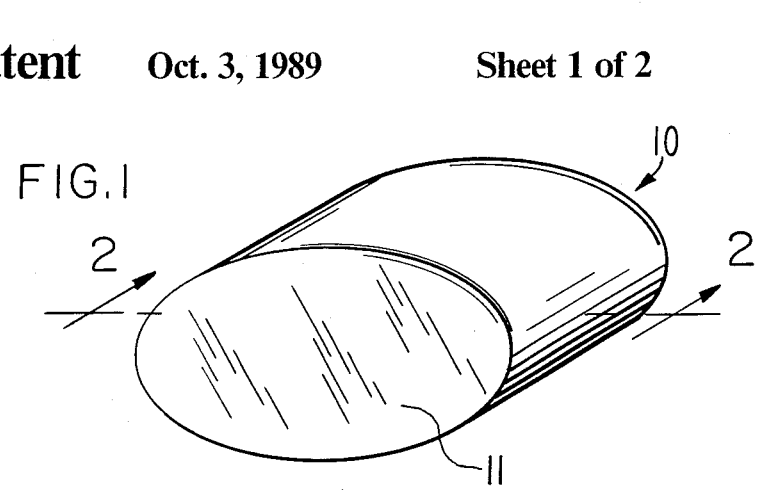
FIG. 1 is a side, elevational view of a dosage form provided by the invention, designed and adapted for orally administering a beneficial drug to the gastrointestinal tract of an animal.
Figure 2:
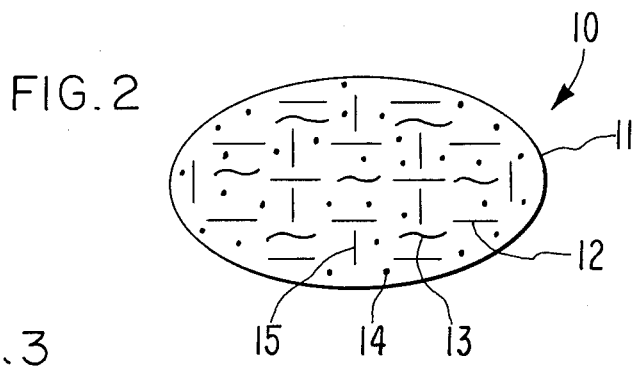
FIG. 2 is a cross-section through 2—2 of FIG. 1 for illustrating the internal structure of the dosage form.

Turning now to the drawing figures in detail, which drawing figures are an example of the dosage forms provided by the invention, and which example is not to be construed as limiting, one example of the dosage form is illustrated in FIG. 1 and in FIG. 2 designated by the numeral 10. In FIG. 1, dosage form 10 comprises a body or matrix 11, which can be manufactured into various sizes and shapes adapted for oral admittance into the gastrointestinal tract of a warm-blooded animal. That is, dosage form 10 can be any convenient shape, such as ellipsoid, bean-shaped, circular shaped, rectangular-shaped, caplet-shaped, and the like.

In FIG. 2, dosage form 10 is seen in cross-section through 2—2 of FIG. 1. In FIG. 2, dosage form 10 comprises a body 11 comprising a cellulosic ether formulation. The cellulosic ether formulation comprised in one presently preferred embodiment a low number average molecular weight hydroxypropylmethylcellulose ether 12, represented by dashes, and a high number average molecular weight hydroxypropylmethylcellulose ether 13, represented by wavy lines. In another preferred embodiment, dosage form 10 comprises a low number average molecular weight hydroxypropylmethylcellulose ether 12, a high number average molecular weight hydroxypropylmethylcellulose ether 13, and a hydroxypropylcellulose 15, represented by vertica lines.

The expression low number average molecular weight as used for the purposes of this invention comprise a cellulosic polymer comprising a low number average molecular weight of from about 9,000 to 30,000. Representative of hydroxypropylmethylcellulose polymers exhibiting a low number average molecular weight of about 9,000 to 30,000 are as follows: (a) a hydroxypropylmethylcellulose having aexhibiting a low number average weight of about 9,000 to viscosity of 3, a degree of polymerization (DP) of 48 and a low number average molecular weight ($MW_n$) of 9,200; (b) a hydroxypropylmethylcellulose having a viscosity of 3, a degree of polymerization of 48 and a low number average molecular weight of 9,600; (c) a hydroxypropylmethylcellulose having a viscosity of 5, a degree of polymerization of 56, and a low number molecular weight of 11,300; (d) a hydroxypropylmethylcellulose having a viscosity of 15, a degree of polymerization of 79, and a number average molecular weight of 15,900; (e) a hydroxypropylmethylcellulose having a viscosity of 35, a degree of polymerization of 102, and a number average molecular weight of 19,600; (f) a hydroxypropylmethylcellulose having a viscosity of 50, a degree of polymerization of 116, and a number average molecular weight of 22,600; (g) a hydroxypropylmethylcellulose having a viscosity of 50, a degree of polymerization of 116, and a number average molecular weight of 23,300; (h) a hydroxypropylmethylcellulose having a viscosity of 100, a degree of polymerization of 145, and a number average molecular weight of 27,800; (i) a hydroxypropylmethylcellulose having a viscosity of 106, a degree of polymerization of 156 and a low number average molecular weight of about 30,000.

The expression "high number average molecular weight" as used for the purpose of this invention comprises a high number average molecular weight of greater than 30,000 to 350,000. Representation of hydroxypropylmethylcellulose ethers exhibiting a high number average molecular weight of from 30,000 to 350,000 are as follows: (a) a hydroxypropylmethylcellulose comprising a viscosity of 1,500, a degree of polymerization of 335 and a number average molecular weight of 65,300; (b) a hydroxypropylmethylcellulose ether comprising a viscosity of 4,000, a degree of polymerization of 460 and a high number average molecular weight of 88,300; (c) a hydroxypropylmethylcellulose comprising a viscosity of 4,000, a degree of polymerization of 460 and a number average molecular weight of 92,500; (d) a hydroxypropylmethylcellulose ether comprising a viscosity of 15,000, a degree of polymerization of 690 and a number average molecular weight of 132,500; (e) a hydroxypropylmethylcellulose ether comprising a viscosity of 30,000, a degree of polymerization of 860 and a number average molecular weight of 165,100; (f) a hydroxypropylmethylcellulose comprising a viscosity of 100,000, a degree of polymerization of 1,260 and a number average molecular weight of 241,900; (g) a hydroxypropylmethylcellulose comprising a viscosity of 220,000, a degree of polymerization of 1,600 and a number average molecular weight of 307,200. Viscosity is related to number average molecular weight and is determined from measurements on aqueous solutions of the cellulosic polymer.

The expression "hydroxypropylcellulose" as used for the purpose of this invention comprises a low substituted hydroxypropylcellulose 15 having a hydroxypropyl content of 7 to 16%. More specific hydroxypropylcellulose ethers comprise a hydroxypropyl content of 7 to 10%, a hydroxypropyl content of 10 to 13%, and a hydroxypropyl content of 13 to 16%.

In one presently preferred embodiment dosage form 10 provided by this invention comprises from 30% to 99.9% of a cellulose ether composition. This cellulose ether composition comprises from 5 to 80% of a low number average molecular weight cellulose ether and from 15 to 90% of a high number average molecular weight hydroxypropylmethylcellulose ether. Dosage form 10 in another embodiment comprises from 30 to 99.9% of a cellulosic ether composition which composition comprises from 5 to 80% of a low number average molecular weight hydroxypropylmethylcellulose, from 10 to 90% of a high number average molecular weight hydroxypropylmethylcellulose ether and 2 to 30% of a low substituted hydroxypropylcellulose. Dosage form 10 comprises from 0.1 to 70% of drug 14, and other optional dosage form 10 forming ingredients, with all the ingredients in dosage form 10 equal to 100%.

Dosage form 10 comprises beneficial drug 14. In the present specification the term "drug" includes any physiologically or pharmacologically active substance that produces a local or systemic effect in animals, including warm-blooded mammals, humans and primates; avians; household, sport and farm animals; laboratory animals; fishes, reptiles and zoo animals. The term "physiologically", as used herein, denotes the administration of a drug to produce generally normal levels and functions in a warm-blooded animal. The term "pharmacologically" generally denotes variations in response to the amount of drug administered to the host. See *Stedman's Medical Dictionary*, 1966, published by Williams and Wilkins, Baltimore, MD.

The active drug that can be delivered includes inorganic and organic compounds without limitation, including drugs that act on the peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, organ systems, reproductive system, skeletal system, autacoid systems, alimentary and excretory systems, inhibitory or autocoids and histamine systems. The active drug that can be delivered for acting on these recipients include anticonvulsants, analgesics, anti-parkinsons, anti-inflammatories, anesthetics, antimicrobials, antimalarials, anti-parasitic, anti-hypertensives, angiotensin converting enzyme inhibitor, antihistamines, antipyretics, alpha-adrenergic agnoist, alpha-blockers, biocides, bactericides, bronchial dilators, beta-adrenergic stimulators, beta-adrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, opthalmics, psychic energizers, parasympathomimetics, sedatives, sympathomimetics, tranquilizers, urinary tract drugs, vaginal drugs, vitamins, and the like.

Exemplary drugs that are very soluble in water can be delivered by dosage form 10 of this invention include prochlorperazine edisylate, ferrous sulfate, aminocaproic acid, potassium chloride, mecamylamine hydrochloride, procainamide hydrochloride, amphetamine sulfate, benzphetamine hydrochloride, isoproteronol sulfate, methamphetamine hydrochloride, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, cimetidine hydrochloride, theophylline cholinate, cephalexin hydrochloride, and the like.

Exemplary drugs that are poorly soluble in water and that can be delivered by dosage form 10 of this invention include diphenidol, meclizine hydrochloride, prochlorperazine maleate, phenoxybenzamine, thiethylperazine maleate, anisindone, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, esterogenic, progestational, corticosteroids, hydrocortisone, hydrocorticosterone acetate, cortisone acetate, triamcinolone, methyltesterone, 17-beta-estradiol, ethinyl estradiol, prazosin hydrochloride, ethinyl estradiol 3- methyl ether, pednisolone, 17-alpha-hydroxyprogesterone acetate, 19-norprogesterone, norgestrel, norethindrone, norethindrone, norethindrone, progesterone, norgesterone, norethynodrel, and the like.

Examples of other drugs that can be delivered by dosage form 10 include aspirin, indomethacin, naproxen, fenoprofen, sulindac, indoprofen, nitroglycerin, propranolol, timolol, atenolol, alprenolol, cimetidine, clonidine, imipramine, levodopa, chloropromazine, methyldopa, dihydroxyphenylalanine, pivaloyloxyethyl ester of alpha-methyldopa, theophylline, calcium gluconate, ketoprofen, ibuprofen, cephalexin, erythromycin, haloperidol, zomepirac, ferrous lactate, vincamine, diazepam, catopril, phenoxybenzamine, nifedipine, diltiazem, milrinone, madol, quanbenz, hydrochlorothiazide, and the like. The beneficial drugs are know to the art in *Pharmaceutical Sciences*, 14th Ed., edited by Remington, (1979) published by Mack Publishing Co., Easton, PA; *The Drug, The Nurse, The Patient, Including Current Drug Handbook*, by Falconer et al., (1974–1976) published by Sunder Co., Philadelphia, PA; *Medicinal Chemistry*, 3rd Ed., Vol. 1 and 2, by Burger, published by Wiley-Interscience, New York and in *Physicians' Desk Reference*, 38 Ed., (1984) published by Medical Economics Co., Oradell, NJ.

The drug in dosage form 10 can be in various forms, such as uncharged molecules, molecular complexes, pharmacologically acceptable salts such as hydrochloride, hydrobromide, sulfate, laurate, palmitate, phosphate, nitrate, borate, acetate, maleate, tartrate, oleate and salicylate. For acidic drugs, salts of metals, amines or organic cations, for example, quaternary ammonium can be used. Derivatives of drugs such as ester, ethers and amides can be used. Also, a drug that is water insoluble can be used in a form that is a water soluble derivative thereof to serve as a solute, and on its release from the device is converted by enzymes, hydrolyzed by body pH or other metabolic processes to the original biologically active form.

Drug 14 can be present in dosage form 10 neat or, as in a presently preferred optional embodiment, with a binder, dispersant, wetting agent, lubricant, or dye. Representative of these include acacia, agar, calcium carrageenan, alginic acid, algin, agarose powder, colloidal magnesium silicate, pectin, gelatin, and the like; binders like polyvinyl pyrrolidone; lubricants such as magnesium stearate; wetting agent such as fatty amines, fatty quaternary ammonium salts; esters of sorbitol, and the like. The phrase drug formulation indicates the drug is present in dosage form 10 neat or accompanied by a binder, and the like. The amount of beneficial drug in dosage form 10 generally is from about 0.05 ng to 5 g or more, with individual dosage form 10 comprising for example, 25 ng, 1 mg, 5 mg, 10 mg, 25 mg, 250 mg, 750 mg, 1.0 g, 1.2 g, 1.5 g, and the like. The dosage form can be administered once, twice or three times a day.

Dosage form 10 is manufactured from a well-mixed composition of dosage-forming members. For example, a particular dosage form is made as follows: first, each of the ingredients comprising a dosage form are independently screened and then blended together, except for the lubricant. Then the homogeneous blend is wet granulated by adding a solvent such as anhydrous ethanol, and the wet ingredients mixed until a uniform blend is obtained by said process. Next, the wet blend is passed through a screen and dried to evaporate the solvent. The resulting granules are passed again through a sieve. Next, a small amount of a finely divided lubricant is added to the dry granules and the lubricant and granules blended to provide a uniform blend. Then, the dosage forming composition is fed to the hopper of a compression machine, and the composition pressed into a dosage form. Typically, about two tons of pressure are applied to yield the final dosage form.

The dosage form can be made also by a dry granulation process of manufacture. The dry process comprises first mixing all the dosage forming ingredients, except for the lubricant, passing the mixed ingredients through a grinding mill to a small mesh size, and then transferring the sized powder to a dry compactor. The compactor densifies the powder, which dense powder is then passed through a sizing mill to regrind the composition. The composition is ground to a small size, typically 20 mesh or smaller. Finally, a dry lubricant is added and the ingredients blended to produce the final dosage forming composition. Then, the composition is fed to a compaction press and compressed into the dosage form 10.

Other standard manufacturing procedures can be used to form the dosage form. For example, the various ingredients can be mixed with a solvent by ballmilling, calendering, stirring or rollmilling, and then pressed into a preselected sized and shaped dosage form 10.

Exemplary solvents suitable for manufacturing the dosage form include inorganic and organic solvents that do not adversely harm the dosage form. The solvents broadly include a member selected from the group consisting of alcohols, ketones, esters, ethers, aliphatic hydrocarbons, halogenated solvents, cycloaliphatic solvents, aromatic, heterocyclic solvents, and mixtures thereof. Typical solvents include acetone, diacetone, methanol, ethanol, isopropyl alcohol, butyl alcohol, methyl acetate, ethyl acetate, isopropyl acetate, n-butylacetate methyl isobutyl ketone, methyl propyl ketone, n-hexane, n-heptane, methylene dichloride, ethylene dichloride, propylene dichloride, ethyl ether, mixtures such as acetone and ethanol, acetone and methanol, methylene dichloride and methanol, ethylene dichloride and methanol, and the like.

The following examples illustrate means and methods for carrying out the present invention. The examples are merely illustrative and they should not be considered as limiting the scope of the invention, as these examples and other equivalents thereof will become more apparent to those versed in the pharmaceutical dispensing art in the light of the present disclosure, the drawings and the accompanying claims.

EXAMPLE 1

Figure 3:
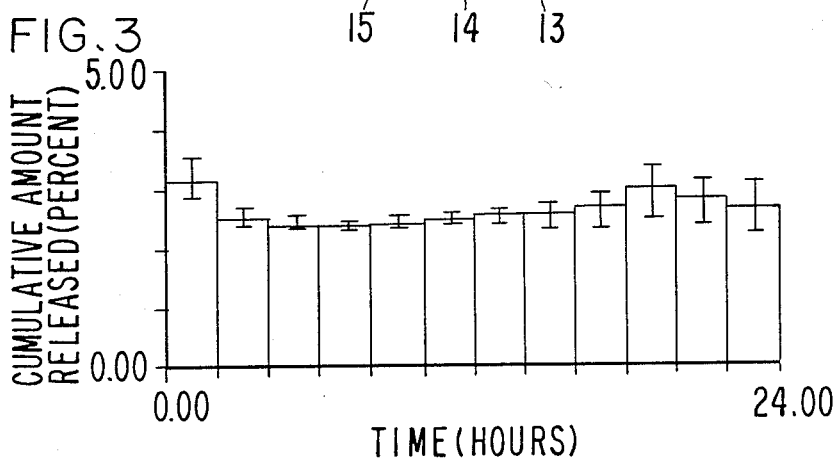
FIGS. 3, 4, 5 and 6 are graphs that depict release rate pattern for dosage forms provided by the invention.
Figure 4:
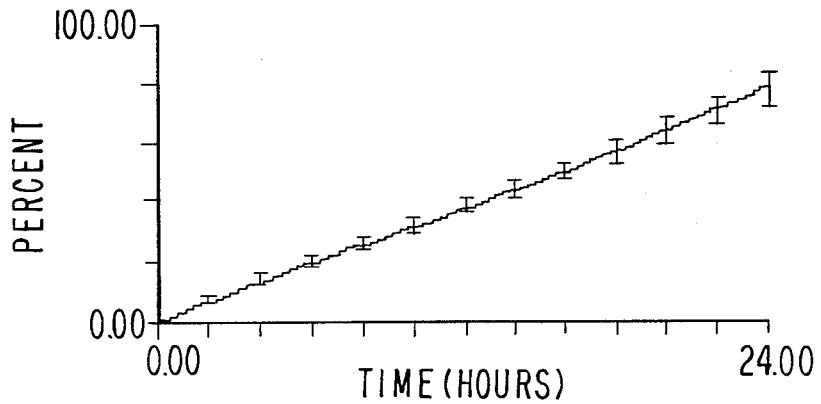

A dosage form 10 comprising 29.5% isosorbide dinitrate (5,900 g); 29.5% lactose (5,900 g); 20% hydroxypropylmethylcellulose ether (4,000 g) exhibiting a low 27,800 number average molecular weight and 20% hydroxypropylmethylcellulose ether (4,000 g) exhibiting a high 88,300 number average molecular weight, were presieved through a 40 mesh screen. The presieved ingredients were mixed in a twin shell blender for 15 minutes and then transferred to a Hobart® mixer. Next, anhydrous methyl alcohol was added slowly with mixing to form a uniform dough. The dough was passed through a 20 mesh screen and then air dried for 2 hours at room temperature. The resulting granules were repassed through the 20 mesh screen and dried at ambient conditions overnight. Then, magnesium stearate, 1%, (200 g), was passed through an 80 mesh per inch screen and then was blended into the mixture in a twin shell mixer for 3 minutes. The resulting granulation was compressed on a D3B Manesty® Press at 2 tons pressure using a 13/32 inch, (1.0 mm) round standard concave punch. The dosage form 10 provided by the manufactured weight 271 mg, comprising 54.2 mg of the hydroxypropylmethylcellulose ether having the low number average molecular weight of 27,800; 54.2 mg of the hydroxypropylmethylcellulose having the high molecular number average molecular weight of 88,300; and 80 mg of isosorbide dinitrate. The dosage forms were placed in artificial gastric fluid and the release of drug measured from the dosage form. The results of the test indicated 78% of the drug was delivered in a 24 hour period at an average delivery rate of isosorbide dinitrate of 2.5 mg per hour. Accompanying FIG. 3 depicts the release rate pattern for the dosage form and accompanying FIG. 4 depicts the cumulative amount released over a prolonged period of 24 hours.

EXAMPLE 2

A dosage form 10 comprising 15% of the enzyme inhibitor captopril, 5% of a low 9,200 number average molecular weight hydroxypropylmethylcellulose, 78% of a high 88,300 molecular weight hydroxypropylmethylcellulose and 2% of stearic acid was prepared as follows: first, 1,500 g of the enzyme inhibitor, 500 g of the low number average molecular weight hydroxypropylmethylcellulose, and 7,800 g of the high molecular weight hydroxypropylmethylcellulose are presieved through a 40 mesh screen and mixed for 15 minutes in a twin shell blender, and the resulting mixture transferred to a Hobart® blender. Then, anhydrous ethanol was added slowly with mixing to form a damp mass. The ethanol alcohol damp mass was passed through a 20 mesh screen and air dried overnight. The dry product was repassed through a 20 mesh screen. The resulting granules were lubricated with 200 g of stearic acid by passing the stearic acid through an 80 mesh screen over the granules and mixing the granules in a twin shell blender for 3 minutes. Next, the resulting granulation was compressed into dosage form using a Manesty press fitted with a standard concave round die of ⅜ inch (0.95 mm) diameter under a compression head of 2 tons. The dosage forms weighed 334 mg and contained 50 mg of captopril.

EXAMPLE 3

Figure 5:
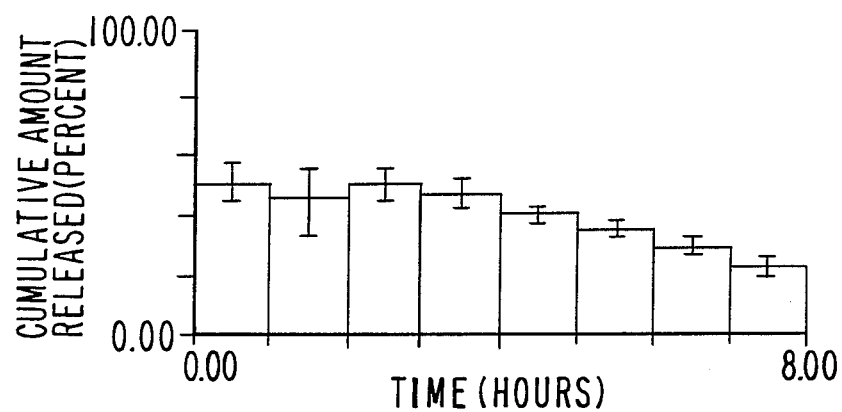
Figure 6:
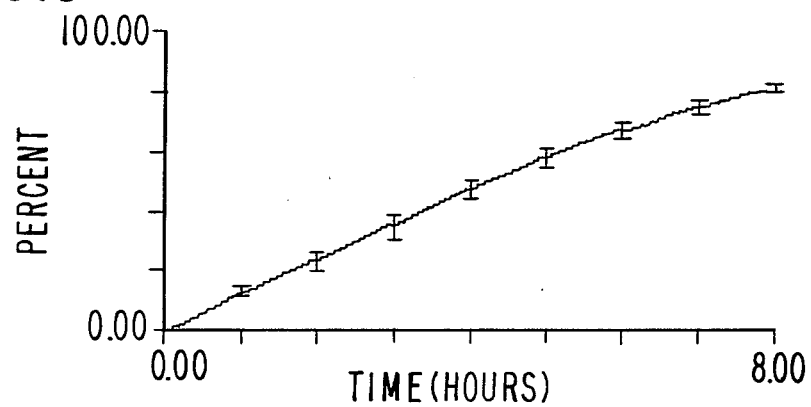

A dosage form 10 was prepared by following the procedure of Example 2. The dosage form of this example comprises 53% ibuprofen; 20% of a hydroxypropylmethylcellulose having a number average molecular weight of 9,200; 20% of a hydroxypropylmethylcellulose having a number average molecular weight of 241,900; 5% hydroxypropylmethylcellulose, and 2% magnesium stearate. The drug release rate pattern for this dosage form is seen in FIG. 5 and the cumulative amount released over a prolonged period of time is seen in FIG. 6.

EXAMPLES 4 to 9

The procedures described above are followed for manufacturing dosage forms comprising the following drugs and the cellulosic ethers: (a) 120 mg of propanol hydrochloride and 40 wt % of a cellulosic ether formulation comprising 20 wt % hydroxypropylmethylcellulose having a nunber average molecular weight of 241,900 and 20 wt % of a hydroxypropylmethylcellulose having a number average molecular weight of 9,200; (b) a dosage form comprising 50 mg of hydrochlorothiazide and 60 wt % of a cellulosic ether formulation comprising 20 wt % hydroxypropylmethylcellulose having a molecular weight of 132,500 and 40 wt % of a hydroxypropylmethylcellulose having a molecular weight of 9,200 ; (c) a dosage form comprising 75 mg of dipyridamole and 60 wt % of a cellulosic ether composition comprising 20 wt % of a hydroxypropylmethylcellulose having a number average molecular weight of 88,300 and 40 wt % of a hydroxypropylmethylcellulose having a number average molecular weight of 27,800; (d) a dosage form comprising 100 mg of verapamil hydrochloride and 50 wt % of a hydroxypropylmethylcellulose having a number average molecular weight of 307,200 and 15 wt % of a hydroxypropylmethylcellulose having a number average molecular weight of 19,600; (e) a dosage form comprising 50 mg of codeine phosphate, 60 wt % of a hydroxypropylmethylcellulose having anumber average molecular weight of 241,900 and 15 wt % of a hydroxypropylmethylcellulose having a number average molecular weight of 9,200; (f) a dosage form comprising 200 mg of mitrofurantoin, 15 wt % of a hydroxypropylmethylcellulose having a number average molecular weight of 241,900 and 45 wt % of a hydroxypropylmethylcellulose having a number average molecular weight of 19,600.

EXAMPLES 10 to 15

The procedures described above are followed for manufacturing dosage forms comprising the following drugs and cellulosic ether formulation: (g) 250 mg of tetracycline; 5 wt % of hydroxypropylmethylcellulose having a number average molecular weight of 132,500; and, 10 wt % of hydroxypropylmethylcellulose comprising a number average molecular weight of 241,900; and 40 wt % of a hydroxypropylmethylcellulose comprising a number average molecular weight of 9,200; (h) 300 mg of cimetidine; 5 wt % of hydroxypropylmethylcellulose having a number average molecular weight of 88,300; 25 wt % of hydroxypropylmethylcellulose comprising a number average molecular weight of 241,900; and, 10 wt % of a hydroxypropylmethylcellulose comprising a number average molecular weight of 9,200; (i) 160 mg of nadolol; 20 wt % of hydroxypropylmethylcellulose having a number average molecular weight of 88,300; 5 wt % hydroxypropylmethylcellulose comprising a number average molecular weight of 307,200; and, 40 wt % of a hydroxypropylmethylcellulose comprising a number average molecular weight of 9,200; (j) 300 mg of quinidine gluconate; 20 wt % of hydroxypropylmethylcellulose having a number average molecular weight of 241,900; 20 wt % of hydroxypropylmethylcellulose comprising a number average molecular weight of 307,200; and, 20 wt % of a hydroxypropylmethylcellulose comprising a number average molecular weight of 9,200; (k) 30 mg of morphine sulfate; 60 wt % of hydroxypropylmethylcellulose having a number average molecular average weight of 132,500; 20 wt % of hydroxypropylmethylcellulose comprising a number average molecular weight of 307,200; and, 10 wt % of a hydroxypropylmethylcellulose comprising a number average molecular weight of 9,200; and, (l) 20 mg of nifedipine; 5 wt % of hydroxypropylmethylcellulose having a number average molecular weight of 132,500; 10 wt % of hydroxypropylmethylcellulose comprising a number average molecular weight of 241,900; and, 75 wt % of a hydroxypropylmethylcellulose comprising a number average molecular weight of 9,200.

EXAMPLES 16 to 21

The procedures described above are followed for manufacturing dosage forms comprising the following drugs and cellulosic ether formulation: (m) 250 mg of erthromycin stearate; 15 wt % of hydroxypropylmethylcellulose having a number average molecular weight of 241,900; 15 wt % of hydroxypropylmethylcellulose comprising a number average molecular weight of 9,200; and, 5 wt % of a hydroxypropylmethylcellulose comprising a hydroxypropoxy content of 7 to 10%; (n) 12 mg of chlorpheniramine maleate; 70 wt % of hydroxypropylmethylcellulose having a number average molecular weight of 241,900; 20 wt % of hydroxypropylmethylcellulose comprising a number average molecular weight of 9,600; and, 5 wt % of a hydroxypropylmethylcellulose comprising a hydroxypropoxy content of 10 to 16%; (o) 8 mg of brompheniramine maleate; 70 wt % of hydroxypropylmethylcellulose having a number average molecular weight of 241,900; 20 wt % of hydroxypropylmethylcellulose comprising a number average molecular weight of 19,600; and, 5 wt % of a hydroxypropylcellulose consisting of a hydroxypropoxy content of 13 to 16%; (p) a dosage form comprising 8 mg of chlorpheniramine maleate; 120 mg of pseudoephedrine sulfate; 25 wt % of hydroxypropylmethylcellulose consisting of a number average molecular weight of 241,900; 25 wt % of hydroxypropylmethylcellulose consisting of a number average molecular weight of 27,800; and, 10 wt % hydroxypropylcellulose consisting of 10 to 13% hydroxypropoxy; and (q) 150 mg of ranitidine hydrochloride; 35 Wt % of hydroxypropoxymethycellulose having a number average molecular weight of 241,900; 15 wt % of hydroxypropoxymethylcellulose consisting essentially of a low number average molecular weight of 19,600; and, 15 wt % hydroxypropylcellulose consisting of 13 to 16 hydroxypropoxy content.

Dosage form 10 provided by the invention makes available a drug delivery matrix suitable for retention in the stomach for gastric retention over the drug releasing life time of the dosage system. Also, when all the drug is released, the system bioerodes into innocuous particles and dissolved polymers that pass from the gastrointestinal tract. The dosage form of the invention comprising higher concentrations of cellulosic ether formulations exhibit better mechanical integrity and they better withstand the abrasive fluidic action of the gastrointestinal tract. The dosage form of the invention provides a broader range of erosion rates including decreased and increased erosion rates in its use of low and high number average molecular weight blends of cellulosic ethers. Another advantage provided by dosage form 10 resulting from its use of high number average molecular weight cellulose ethers is that it provides more physical stability, improved resistance to thermal shock and it helps lessen the incidence of matrix cracking over storage time, when stored in fluctuating ambient temperature conditions. Also, the dosage forms use of the high number average molecular weight cellulosic ethers exhibit decreased tackiness in high humidity thereby preventing sticking of one to another. The use of high number average molecular weight cellulose ethers provides more rate control of the drug administration over time. The use of the cellulose ethers, especially the high number average molecular wt cellulose ethers which swell extensively when hydrated, lessens direct drug contact with mucosal tissues and thereby lessens the incidence of tissue irritation for irritating drugs.

The novel dosage form of this invention comprises means for the obtainment of precise release rates in the environment of use while simultaneously providing beneficial therapy to a recipient. While there has been described and pointed out features of the invention as applied to presently preferred embodiments, those skilled in the dispensing art will appreciate that various modifications, changes, additions and omissions in the dosage form ilustrated and described can be made without departing from the spirit of this invention.

We claim:

1. A dosage form for delivering a beneficial drug to an environment of use, which dosage form comprises: a matrix adapted for entrance into the environment of use, said matrix comprising from 30 to 99.9% of a cellulosic ether formulation, which formulation comprises from 10 to 99% of at least one hydroxypropylmethylcellulose comprising a high number average molecular weight of from 30,000 to 350,000, from 5 to 80% of at least one hydroxypropylmethylcellulose comprising a low number average molecular weight of from 9,000 to 30,000, from 2 to 30% of a hydroxypropylcellulose comprising a hydroxypropoxy content of 7 to 16%, and a dosage amount of the beneficial drug.

2. The dosage form for delivering the beneficial drug to the environment of use, according to claim 1, wherein the environment of use is the fluidic gastrointestinal tract of a warm-blooded animal.

3. The dosage form for delivering the beneficial drug to the environment of use, according to claim 1, wherein the environmemt of use is the human stomach.

* * * * *